United States Patent [19]

Fukano et al.

[11] Patent Number: 4,529,711

[45] Date of Patent: Jul. 16, 1985

[54] FLUID BLOOD COAGULATION PROMOTER

[75] Inventors: Yoshimasa Fukano; Susumu Wada, both of Ichihara, Japan

[73] Assignee: Toray Silicone Company, Ltd., Tokyo, Japan

[21] Appl. No.: 505,674

[22] Filed: Jun. 20, 1983

Related U.S. Application Data

[62] Division of Ser. No. 331,851, Dec. 17, 1981, abandoned.

[30] Foreign Application Priority Data

Dec. 24, 1980 [JP] Japan .................. 55-183084

[51] Int. Cl.³ .................. G01N 1/28; G01N 33/48
[52] U.S. Cl. .................. 436/177; 210/927; 436/69; 556/439; 556/449
[58] Field of Search .................. 436/177, 69; 210/927; 73/64.1; 556/439, 449

[56] References Cited

FOREIGN PATENT DOCUMENTS

| | | | |
|---|---|---|---|
| 2453813 | 5/1976 | Fed. Rep. of Germany | 73/64.1 |
| 28495 | 3/1978 | Japan | 210/927 |
| 44056 | 4/1981 | Japan | 210/927 |
| 129860 | 10/1981 | Japan | 73/64.1 |

*Primary Examiner*—Arnold Turk
*Attorney, Agent, or Firm*—Robert L. McKellar

[57] ABSTRACT

What is disclosed is a composition of matter useful in expediting the coagulation of whole blood. The coagulation promoter is a polysiloxane which contains at least one hydroxy functional or carboxylic functional monovalent hydrocarbon radical bonded to a silicon atom.

17 Claims, No Drawings

FLUID BLOOD COAGULATION PROMOTER

This application is a divisional application of U.S. Ser. No. 331,851, filed Dec. 17, 1981, now abandoned.

BACKGROUND OF THE INVENTION

This invention relates to a blood coagulation promoter.

When blood chemistry tests are conducted using blood as the test material, the general practice is to first coagulate the blood and then to centrifuge the blood to separate the unclotted component, namely the blood serum, which is then used as sample material for the tests.

Coagulation of blood is a phenomenon which is a combination of various complex processes involving various biochemical factors, but the general understanding is that insoluble proteins in the form of fibrin formed from thrombin and fibrinogen participate in the process.

The clotting time of blood, in other words the coagulation time of fibrins, is commonly measured by the method of Lee and White (*Clinical Diagnosis by Laboratory Methods*, 12th edition, W. B. Saunders Co., (1954), page 176). The Lee-White method performed in glass test tubes can be completed in 5–15 minutes, while a surface baking treatment using dimethyl polysiloxane fluid performed in glass test tubes or plastic or aluminum test tubes requires approximately 30 minutes. On the other hand, the actual time required for blood to coagulate completely to allow clean separation into serum and blood clot suitable for use in various tests, is much longer than the time measured by the Lee-White method and is of the order of 1–2 hours.

The delay in blood clotting or the long time required for blood to coagulate completely is a fairly serious problem today when blood tests have been speeded up by the introduction of automation and the associated need to make more efficient use of the test functions while, at the same time, there is the possibility of changes taking place with time in the different components in the blood, casting doubts on the accuracy of the tests.

A practice for the separation of serum known in the prior art was the use of a gel-like material. For example, Japanese Patent Applications No. [1974]-89389, No. [1975]-40198, and No. [1977]-74657 describe the use of a dimethylpolysiloxane fluid and silica mixture in gel form to make this type of separation.

These prior art gel-like materials possessed the necessary fluidity, during centrifugal separation, to migrate to the interface of the layers being separated, making it possible to decant the supernatant layer at the end of centrifugation without disturbing the separated supernatant. On the other hand, when the prior art gel-like material is placed in the blood collecting tube before collecting blood, and blood was then sampled and centrifuged, as is the practice in this "floating-up" method, there was a delay in blood clotting, especially in glass tubes, under certain conditions, which was of the same order or even worse than that experienced in nonglass equipment. There is also the disadvantage that the time required for the blood to settle is extremely long. If centrifugal separation is hurried, before the blood has had ample time to coagulate completely, the blood serum collected would be unsatisfactory. This problem has been particularly serious during recent years because of the increasing use of disposable test tubes made of plastic. The inventors researched the problem of time delay in the coagulation process particularly when a silicone material is used as a separating agent and have arrived at this invention.

THE INVENTION

This invention therefore proposes a blood coagulation promoter. The invention relates to a blood coagulation promoter whose principal component is an organopolysiloxane which has at least one carboxylic acid functional monovalent hydrocarbon group or hydroxyl functional monovalent hydrocarbon group per molecule. This invention therefore consists of a blood coagulation promoter consisting of an organopolysiloxane fluid containing at least one functional group selected from the group consisting of (A) a hydroxy functional monovalent hydrocarbon radical bonded to a silicon atom and (B) a carboxylic acid functional monovalent hydrocarbon radical bonded to a silicon atom wherein the promoter has a viscosity of 0.001 to 500 Pa·s at 25° C.

The inventors discovered that contacting blood with these organopolysiloxanes caused blood coagulation to be expedited.

In explaining this behavior, the organopolysiloxane fluid, which is the principal agent of the blood coagulation promoter in this invention, is characterized by the presence of at least one monovalent hydrocarbon group incorporating a hydroxyl group or a carboxyl acid group per molecule of polysiloxane, and this feature imparts the blood coagulation promoting property which is not shown by the prior art polysiloxanes.

At least one hydroxyl or carboxylic acid group has to be present per monovalent hydrocarbon radical, and both hydroxyl and carboxylic acid groups may be on the same molecule.

The hydroxy functional or carboxylic acid functional monovalent hydrocarbon radicals can be modified alkyl radicals, cycloalkyl radicals, phenyl radicals, or aralkyl radicals. Modified alkyl radicals, particularly the propyl radical is the one preferred, i.e., $-(CH_2)_3OH$.

Other specific examples of the hydroxyl functional monovalent hydrocarbon radicals include

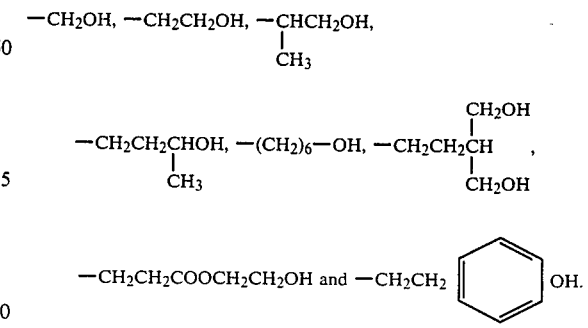

Specific examples of the carboxylic acid functional monovalent hydrocarbon groups are

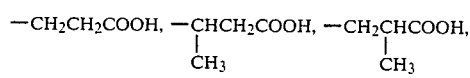

-continued

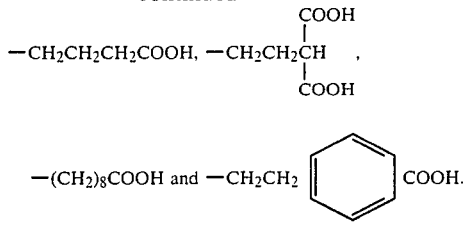

The hydroxyl functional or carboxylic acid functional monovalent hydrocarbon radical should be present in a ratio of at least one of these groups per organopolysiloxane molecule, and there is no specific upper limit to this number per molecule, but the general practice is not to exceed 50 mol% of the total of silicon bonded organic groups. Monovalent hydrocarbon groups within this organopolysiloxane which do not have hydroxyl or carboxyl groups can be represented by aralkyl groups, allyl groups, alkynyl groups, or halogenated alkyl groups among the many well-known radicals which can be present. Other groups include the methyl group, ethyl group, phenyl group, 2-phenyl-ethyl group, octyl group, vinyl group, and the 3,3,3-trifluoropropyl group.

The organopolysiloxane liquid is a straight chain, branched chain, cyclic or three dimensional network, and there is no special limitation to its degree of polymerization except that its construction and degree of polymerization must allow the polymer to be a liquid at ordinary room temperature.

The viscosity of the organopolysiloxane fluids of this invention should be from 0.001 to 500 Pa·s at 25° C. and a viscosity in the range 0.01 to 50 Pa·s is desirable and a viscosity in the range of 0.01 to 1 Pa·s is particularly desirable.

The general formulae of some organopolysiloxanes useful in this invention are shown below.

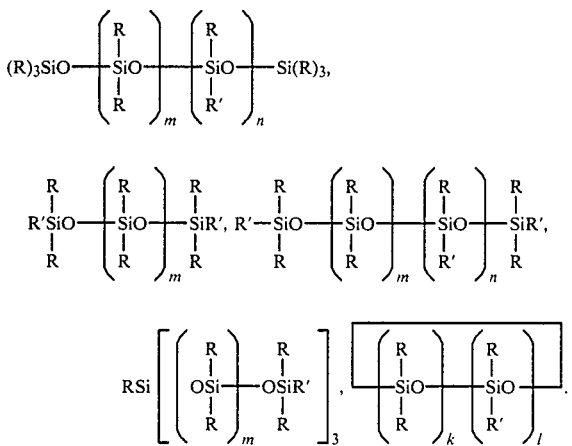

For purposes of this invention, R' is hydroxyl or carboxylic acid functional monovalent hydrocarbon radical; R is a monovalent hydrocarbon radical with no hydroxyl or carboxylic acid groups; m is 0 or an integer of at least 1; n is an integer of at least 1; k has value of 1, 2, or 3, and l is an integer of 1 to 4 with the limitation that $k+l=4$.

This organopolysiloxane fluid can be readily prepared by adding a vinyl group-containing alcohol or a vinyl group-containing carboxylic acid group to organohydrodiene polysiloxane, or to silicon bonded hydrogen containing silanes, organosilanes, or organopolysiloxanes followed by homopolymerization of the addition product or copolymerization of the addition product with some other silanes, organosilanes, or organopolysiloxanes.

In such a situation the presence of any residual silicon bonded hydrogen atoms does not offer any impediment to the objective of this invention.

Methods by which the inventive organopolysiloxane fluid is contacted with blood include (1) placement of a small quantity of the inventive organopolysiloxane into the blood sampling tube or adding a few drops after which blood is placed over it, (2) coating the walls of the blood sampling tube beforehand with the inventive organopolysiloxane fluid followed by the introduction of blood, and (3) adding a few drops of organopolysiloxane to the already collected blood. The inventive organopolysiloxane may be contacted with blood by itself or it can be mixed with some other components. The other components can be liquid or solid. When a solid is used, a powder, and particularly a very fine silica powder filler, for example 10 mμ silica, is especially suitable. A gel-like material composed of the inventive organopolysiloxane, and very fine silica powder (Aerosil R 972 manufactured by DeGussa, West Germany—10 mμ average size) mixture with a density intermediate between blood serum and blood clot, is a very desirable blood coagulation promoter.

This gel-like material is first placed at the bottom of the blood collection tube, and blood is collected into said blood collection tube and then centrifuged, and the gel-like material will float up and occupy the section between the serum and clot to form a barrier, making it very simple to remove the serum. It is also possible to collect blood into the blood sampling tube first and then adding the gel-like material from a disperser into the blood collecting tube, then centrifuging the tube, whereupon the gel-like material will flow into the blood and bring about the desired objective. In such a situation, the inventive organopolysiloxane fluid serves as the blood coagulation promoter and as a separation agent for the separation of the serum from the clot, thereby providing a bifunctional role.

Other liquid components can be incorporated in the inventive organopolysiloxane fluid which are, for example, organic solvents capable of dissolving the organopolysiloxane. The organopolysiloxane can be dissolved in a solvent such as n-hexane or xylene to prepare a 0.01–0.1 wt% solution, which can then be placed in a blood sampling tube. The tube is then shaken to coat the inner walls with this solution.

The quantity of inventive organopolysiloxane which is contacted with blood varies with the method of contact employed, and the use of about 100 mg of polysiloxane per 7–8 ml of blood is standard for methods (1) and (3), while the use of 0.01–0.1 wt% dilution to coat the tube walls is adequate in the case of method (2).

The blood clotting promoter in this invention is effective not only on human blood but also on the blood of cows, pigs, horses and fowl.

When blood collected in a blood sampling tube or blood collecting bag is to have its clotting process accelerated, the blood clotting promoter of this invention is particularly effective when the blood collecting vessel is made of plastic, rubber, or a metal-type non-glass material, or when the inner walls of the vessel have been previously subjected to a baking treatment with dimethylpolysiloxane. When blood is collected in an ordinary glass tube and prior art dimethylpolysiloxane and a gel-like material consisting of silica-type filler is added as a separation agent, followed by centrifugation to separate the serum from clot, the presence of the prior art dimethylpolysiloxane will delay the coagulation of the blood, but when the blood coagulation promoter of this invention is present, this delayed process is negated because the inventive fluid overcomes the effects of the prior art dimethylpolysiloxane.

Some practical examples are presented in which the term "parts" will refer to parts by weight and the viscosity values all refer to values obtained at 25° C. Any use of Me in the chemical formula indicates a methyl radical.

What is referred to as clotting time is the time required from the instant the blood taken into a 15 mm inner diameter and 100 mm long test tube or blood collecting tube is started on its coagulation process to the time when the blood no longer flows when the tube is placed in a horizontal position.

centrifugal acceleration of 1,410 G's for 10 minutes and then collecting the supernatant serum with a pipette.

These examples are not to be construed as limiting the invention as set forth in the claims.

EXAMPLES 1–5

Plastic test tubes (polypropylene resin, polystyrene resin), a glass test tube (borosilicate glass), a glass test tube with the inner walls baked at 250° C. for 1 hour using prior art dimethylpolysiloxane, and a glass test tube with about 1.5 g of a mixture of 100 parts dimethylpolysiloxane fluid of 12.5 Pa·s viscosity and 14.5 parts hydrophobic fine silica powder 10 m$\mu$ placed at the bottom of the tube was prepared. 100 mg of a blood coagulation promoter of this invention was added dropwise to each tube, and 7 ml of whole blood directly after sampling from a healthy male was added to each tube, the mixture was allowed to stand 45 minutes, and it was then subjected to centrifugal separation after which the volume of serum recovered was measured. The results of this study are shown in Table I.

TABLE I

| | Test Tube Material | Coagulation Promoter | Clotting Time | Serum Volume |
|---|---|---|---|---|
| Example 1 | Polypropylene | $Me_3-SiO-[SiO(Me)(Me)]_{96}-[SiO(Me)(CH_2CH_2COOH)]_3-Si-Me_3$<br>Viscosity .32 Pa·s | 5~10 minutes | 3.1 ml. |
| Example 2 | Polystyrene | $Me_3-SiO-[SiO(Me)(Me)]_{50}-[SiO(Me)(CH_2CH_2CH_2OH)]_2-Si-Me_3$<br>Viscosity .12 Pa·s | 6~12 minutes | 3.0 ml. |
| Example 3 | Polystyrene | $HO(CH_2)_3-[SiO(Me)(Me)]_{30}-Si(Me)(Me)(CH_2)_3OH$<br>Viscosity .084 Pa·s | 5~10 minutes | 2.9 ml. |
| Example 4 | Glass Tube With The Gel-like Material | $HOOCCH_2CH_2-[SiO(Me)(Me)]_{14}-Si(Me)(Me)-CH_2CH_2COOH$<br>Viscosity .006 Pa·s | 5~12 minutes | 3.0 ml. |
| Example 5 | Glass Tube With Polydimethylsiloxane Baked Onto Inner Walls | Sample as Example 2 | 6~15 minutes | 3.0 ml. |
| Comparative Example 1 | Polypropylene | None | 25~35 minutes | 1.4 ml. |
| Comparative Example 2 | Polystyrene | None | 26~37 minutes | 1.2 ml. |
| Comparative Example 3 | Glass Tube (With Gel-like Material) | None | 18~27 minutes | 2.8 ml. |
| Comparative Example 4 | Glass Tube (Some Dimethylpolysiloxane Baked Onto Inner Wall) | None | 26~35 minutes | 1.7 ml. |

The quantity of serum was determined by subjecting whole blood in a 15 mm inner diameter and 100 mm long test tube to 2,500 rpm centrifugation for a relative The test tube with gel-like material of Example 4 to which a blood coagulation promoter had been added in dropwise manner was allowed to stand 60 days after which it was used once more in a serum separation test, and there was essentially no change in the blood coagulation time and volume of serum collected. By comparison, the test tube of Comparative Example 3 which also contained gel-like material was allowed to stand 30 days after the initial test and once again subjected to the same coagulation test, whereupon there was a long delay in coagulation time, and it was necessary to let the blood stand an hour before a decent recovery volume of serum could be obtained.

EXAMPLE 6

The blood coagulation agent represented by the following formula

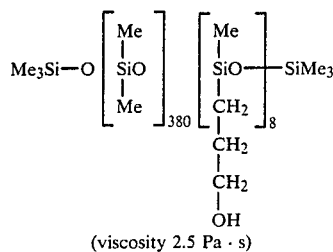

(viscosity 2.5 Pa · s)

was dissolved in xylene to prepare a 0.1 wt% solution, and this solution was placed in a polypropylene test tube to wet the inner surface after which the solution was discarded, and the tube was air dried to remove the xylene.

The blood clotting time and serum volume were determined in the same manner as in Examples 1–5, and the clotting time was 6 to 16 minutes and the volume of serum collected was 3.1 ml.

EXAMPLE 7

One hundred parts of the blood coagulation promoter of Example 6 and 14.5 parts of hydophobic fume silica powder of 130 m²/g surface area were mixed to prepare a uniform mixture, and 1.5 g of the gel-like material having a density of 1.045 were placed at the bottom of a glass blood sampling tube and 7 ml of whole blood from a healthy male was placed in this tube after which the coagulation time was measured and found to be 5–12 minutes. The tube was stoppered after 12 minutes and centrifuged 10 minutes at 2500 rpm. The gel-like material migrated to the intermediate level of the blood sampling tube to form a barrier layer, the serum collected at the upper section of the tube and the clot at the bottom section in a clearly defined two-layered separation. The tube containing the gel-like material was allowed to stand 30 days after which the same test was repeated, whereupon the same type of results were obtained.

In place of the blood coagulation promoter of Example 6, prior art dimethylpolysiloxane of 12.5 Pa·s was used to prepare the gel-like material which was then utilized in the same test, and the coagulation time was 20–31 minutes. The test tube with gel-like material was allowed to stand 30 days after which the same test was repeated whereupon the clotting time was 60–70 minutes.

That which is claimed is:

1. A method of expediting the coagulation of whole blood which consists of contacting whole blood with a blood coagulation promoter consisting of an organopolysiloxane fluid containing at least one functional group selected from the group consisting of
   (A) a hydroxy-functional monovalent hydrocarbon radical bonded to a silicon atom and
   (B) a carboxylic acid functional monovalent hydrocarbon radical bonded to a silicon atom wherein the promoter has a viscosity of 0.001 to 500 Pa·s at 25° C.

2. A method as claimed in claim 1 wherein the blood coagulation promoter has a viscosity in the range of 0.01 to 50 Pa·s at 25° C.

3. A method as claimed in claim 2 wherein the viscosity of the blood coagulation promoter is in the range of 0.01 to 1 Pa·s at 25° C.

4. A method as claimed in claim 1 wherein the blood coagulation promoter has the general formula

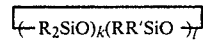

wherein R' is selected from a group consisting of (A) a hydroxyl-functional monovalent hydrocarbon radical and (B) a carboxylic acid functional monovalent hydrocarbon radical; R is a monovalent hydrocarbon radical of 1 to 4 carbon atoms; k has a value of 1, 2, or 3 and l is an integer of 1 to 4 wherein k+l has a total value of 4.

5. A method as claimed in claim 4 wherein in the promoter R is methyl and R' is $-(CH_2)_3OH$.

6. A method as claimed in claim 4 wherein in the promoter R is propyl and R' is $-(CH_2)_3OH$.

7. A method as claimed in claim 1 wherein the blood coagulation promoter has the general formula $R'R_2SiO(R_2SiO)_m(RR'SiO)_nSiR_2R'$ wherein R' is selected from a group consisting of (A) a hydroxyl-functional monovalent hydrocarbon radical and (B) a carboxylic acid functional monovalent hydrocarbon radical; R is a monovalent hydrocarbon radical of 1 to 4 carbon atoms; m is 0 or an integer of at least 1; n is an integer of at least 1.

8. A method as claimed in claim 7 wherein in the promoter R is propyl and R' is $-(CH_2)_3OH$.

9. A method as claimed in claim 7 wherein in the promoter R is propyl and R' is $-(CH_2)_2COOH$.

10. A method as claimed in claim 1 wherein the blood coagulation promoter has the general formula $RSi[(OSiR_2)_m(OSiRR')]_3$ wherein R' is selected from a group consisting of (A) a hydroxyl-functional monovalent hydrocarbon radical and (B) a carboxylic acid functional monovalent hydrocarbon radical; R is a monovalent hydrocarbon radical of 1 to 4 carbon atoms; m is 0 or an integer of at least 1.

11. A method as claimed in claim 10 wherein in the promoter R is methyl and R' is $-(CH_2)_3COOH$.

12. A method as claimed in claim 10 wherein in the promoter R is propyl and R' is $-(CH_2)_2COOH$.

13. A method as claimed in claim 1 wherein the blood coagulation promoter has the general formula $R_3SiO(R_2SiO)_m(RR'SiO)_nSiR_3$ wherein R' is selected from a group consisting of (A) a hydroxyl-functional monovalent hydrocarbon radical and (B) a carboxylic acid functional monovalent hydrocarbon radical; R is a monovalent hydrocarbon radical of 1 to 4 carbon atoms; m is 0 or an integer of at least 1; n is an integer of at least 1.

14. A method as claimed in claim 13 wherein in the promoter R is methyl and R' is $-(CH_2)_3OH$.

15. A method as claimed in claim 13 wherein in the promoter R is methyl and R' is $-(CH_2)_2COOH$.

16. A method as claimed in claim 13 wherein in the promoter R is propyl and R' is $-(CH_2)_3OH$.

17. A method as claimed in claim 13 wherein in the promoter R is propyl and R' is $-(CH_2)_2COOH$.

* * * * *

UNITED STATES PATENT AND TRADEMARK OFFICE
CERTIFICATE OF CORRECTION

PATENT NO. : 4,529,711

DATED : 7-16-85

INVENTOR(S) : Yoshimasa Fukano and Susumu Wada

It is certified that error appears in the above-identified patent and that said Letters Patent is hereby corrected as shown below:

Column 3, line 63

Delete "and 1 is an integer" and

Insert --and $\ell$ is an integer--

Column 8, line 26

Delete "3 and 1"

Insert --3 and $\ell$--

Column 8, line 27

Delete "k + 1"

Insert -- k + $\ell$--

Signed and Sealed this

Eleventh Day of October, 1988

Attest:

DONALD J. QUIGG

*Attesting Officer*  *Commissioner of Patents and Trademarks*